United States Patent [19]

Stjernschantz et al.

[11] Patent Number: 5,510,382
[45] Date of Patent: * Apr. 23, 1996

[54] METHOD AND COMPOSITION FOR TREATMENT OF GASTRIC AND DUODENAL DISORDERS

[75] Inventors: Johan Stjernschantz; Bahram Resul, both of Uppsala, Sweden

[73] Assignee: Pharmacia AB, Uppsala, Sweden

[*] Notice: The portion of the term of this patent subsequent to Jun. 29, 2010, has been disclaimed.

[21] Appl. No.: 57,512

[22] Filed: May 6, 1993

Related U.S. Application Data

[63] Continuation of Ser. No. 733,738, Jul. 23, 1991, Pat. No. 5,223,537.

[51] Int. Cl.$^6$ ............................................. A61K 31/557
[52] U.S. Cl. ............................ 514/530; 514/926; 514/927
[58] Field of Search .......................... 514/530, 926, 514/927

[56] References Cited

U.S. PATENT DOCUMENTS

| | | | |
|---|---|---|---|
| 3,937,801 | 2/1976 | Uppmann | 424/10 |
| 4,820,728 | 4/1989 | Collins | 514/530 |
| 4,833,157 | 5/1989 | Kluender | 514/530 |
| 5,422,368 | 6/1995 | Stjernschantz et al. | 514/530 |

FOREIGN PATENT DOCUMENTS 1324737  7/1973  United Kingdom.

OTHER PUBLICATIONS

Pfitzner (1965); J. Am. Chem. Soc. 87, pp. 5670–5678.
Corey (1966); J. Am. Chem. Soc. 88, p. 5654.
Brown (1972); J. Am. Chem. Soc. 94, pp. 7159–7161.
Vincent et al. "Substituted 11–Deoxy–prostaglandins" Chem Abst 87(5) 39000 FrDemande 2301242 (1976).
Yankee et al. Chem Abstr 88, 62048x, (1978).
Bundy, Chem Abstr 90 168141d, (1979).
Chem Abst. 84:58751, 1975.
Chem Abst. 88:62048, 1978.
Chem Abst. 90:168141, 1979.

*Primary Examiner*—Raymond Henley, III
*Attorney, Agent, or Firm*—Dinsmore & Shohl

[57] ABSTRACT

The invention is related to the field of treating gastric and duodenal disorders and more specifically to the use of certain 13,14-dihydro-prostaglandin E derivatives, especially of $PGE_2$, which are modified to contain a ring structure in the omega chain. The invention relates also to pharmaceutical compositions containing an active amount of these derivatives.

20 Claims, 1 Drawing Sheet

METHOD AND COMPOSITION FOR TREATMENT OF GASTRIC AND DUODENAL DISORDERS

This is a continuation of application Ser. No. 07/733,738, filed Jul. 23, 1991 now U.S. Pat. No. 5,223,537.

This invention is related to the field of treating gastric and duodenal disorders and more specifically to the use of certain 13,14-dihydro-prostaglandin E derivatives, especially of $PGE_2$, which are modified to contain a ring structure in the omega chain. The invention relates also to pharmaceutical compositions containing an active amount of these derivatives.

BACKGROUND

Gastritis, gastric ulcer, duodenal ulcer and reflux gastritis comprise common disorders of the alimentary tract. The etiology behind these disorders is not fully clear but it is believed that mental stress may be a contributing factor. Other factors that may be of importance are dietary factors, too large consumption of coffee, tobacco and alcohol, certain kinds of medication, and anatomical or functional anomalies. Recently it has been demonstrated that a bacteria (*Heliobacter pilori*) is associated with ulcer formation in the ventricle but a clear-cut causative relationship between this bacteria and ulcer formation in the ventricle or duodenum so far has not been established.

Generally, it is believed that the parasympathetic nervous system is important for normal functioning of the ventricle and parasympathectomy by selectively cutting the cholinergic nerve fibres from the regal nerve (selective vagotomy) has been used as a modality of treatment of gastric or duodenal ulcer. The acidity of the gastric juice is due mainly to hydrochloric acid (HCl) secreted by the parietal cells in the gastric mucosa. The main function of HCl is to acidify the gastric juice enough to enable acid hydrolysis of proteins and to activate pepsinogen secreted by the gastric mucosa to pepsin which catalyses the hydrolysis of proteins in the stomach. Too much secretion of HCl is believed to predispose to gastric and particularly duodenal ulcer. The secretion of HCl from the parietal cells is physiologically controlled in a complex way. The parietal cells are receptive to at least four different autacoids, namely acetylcholine, gastrin, histamine and prostaglandins. Particularly prostaglandins of the E type have been shown negatively to affect secretion of HCl. Acetylcholine, gastrin and histamine enhance the secretion of HCl, whereas prostaglandins inhibit or decrease the secretion of HCl. In a particular disease, the Zollinger-Ellison Syndrome, a tumour producing gastrin causes a marked increase in the secretion of gastric acid.

In addition to secretion of HCl, secretion of bicarbonate ($HCO_3^-$) by the gastric mucosa and particularly by the duodenal mucosa is considered important for protecting the local tissue from damage by the gastric juice. Prostaglandins stimulate this secretion of $HCO_3^-$, e.g. in the duodenal mucosa. Prostaglandins, particularly of the E type also effectively stimulate mucus formation. Increased secretion of mucus may have an important protective effect on the mucous membrane in the ventricle as well as in the duodenum.

Gastric ulcers, duodenal ulcers and gastritis are usually treated with antacids (neutralizing agent) and/or antihistamines. Particularly H2 blockers such as cimetidine and ranitidine are effective antiulcer medications Inhibitors of gastrin receptors such as proglumide are also to some extent employed. Recently, the utilization of $H^+/K^+$-ATPase inhibitors has been employed to block gastric secretion. A drug with such activity is omeprazole. Generally, cholinolytic agents are not used but selective vagotomy is employed in some cases. Recently, prostaglandins particularly of the E type, e.g. 16-hydroxy-16-methyl-$PGE_1$-methyl ester (Misoprostol) have been demonstrated to be effective. Prostaglandins have been found to be particularly advantageous when used prophylactically to prevent formation of gastric or duodenal ulcer during therapy with anti-inflammatory drugs, such as aspirin, indomethacin and like agents. Common for these agents is that they inhibit the cyclooxygenase enzyme in the biosynthesis of prostaglandins.

The most likely mechanisms of action of prostaglandins to protect the mucous membrane of the ventricle and duodenum are increased formation of mucus, increased secretion of $HCO_3^-$, as well as an antisecretory effect of prostaglandins on HCl. However, the latter two mechanisms require relatively large amounts of prostaglandins to be present and since clinically such concentrations are not achieved it is generally believed that the main mechanism of exogenous prostaglandins to protect the ventricle and duodenum from ulcer formation is increased mucus formation. A direct cytoprotective effect is also possible. Increased mucus formation is also beneficial with regard to healing of already established ulcers. Endogenous prostaglandins, physiologically released, may also have an important anti-secretory effect as well as an effect on bicarbonate transport.

Prostaglandins of the E type have been found to increase mucus formation in the stomach. Prostaglandins of the E type also markedly increase the blood flow in the ventricle.

A disadvantage of prostaglandin treatment, however, is the relatively frequent occurrence of gastrointestinal side effects. Typically prostaglandins of the E type cause diarrhea. Abdominal pain, dyspepsia, flatulence and nausea may also occur during treatment with prostaglandins. Of these side effects diarrhea and abdominal pain seem to be the most disturbing side effect not infrequently resulting in interruption of the treatment with prostaglandins which seem to be about as effective as H2 blockers in the treatment of gastric and duodenal ulcers but since prostaglandins tend to augment pain sensation, the pain typically experienced by patients suffering from these conditions during prostaglandin treatment is more severe than during the H2 blocking treatment modalities. Therefore, so far prostaglandins of the E type are mostly used prophylactically to prevent formation of gastric and/or duodenal ulcer during therapy with anti-inflammatory agents rather than to treat already established ulcers.

THE PRESENT INVENTION

We have now unexpectedly found that by certain modifications of the prostaglandin E molecule it is possible to eliminate its irritating effect on sensory nerves. It has moreover been found that such PGE-derivatives lacks a diarrheagenic effect.

The prostaglandin derivatives to be used according to the invention are 13,14-dihydro-derivatives of PGE, and especially of $PGE_2$ in which the omega chain contains a ring structure, preferably a phenyl ring.

In copending patent application Ser. No. 469442 the general concept of modifying the omega chain of prostaglandins A, B, E and F, is disclosed. The derivatives were found to exhibit excellent properties for use in the treatment of glaucoma or ocular hypertension.

The derivatives to be used in a method for treating a person having duodenal or gastric ulcer, gastritis or related alimentary diseases have the general structure:

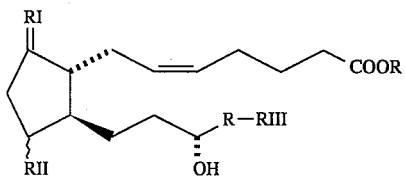

wherein

R is an alkyl chain with 1–10 carbon atoms, especially with 1–6 carbon atoms

RI is O or $CH_2$

RII is H, OH, lower alkyl, preferably with 1–3 carbon atoms, halogen, preferably Cl, Br and F X is carbon chain with 1–9, preferably 1–6, and more specifically 2–6, such as 2, 3, 4, 5, or 6 atoms in the chain, optionally interrupted by one heteroatom O, N or S RIII is a ring structure selected from the group consisting of a phenyl group which is unsubstituted or has one or more substituents selected from C1–C5 alkyl groups, C1–C4 alkoxy groups, trifluoromethyl groups, C1–C3 aliphatic acylamino groups, nitro groups, halogen atoms, and a phenyl group; or an aromatic heterocyclic group having 5–6 ring atoms, like thiazol, imidazole, pyrrolidine, thiopene and oxazole; or a cycloalkane or a cycloalkene with 3–7 carbon atoms in the ring, optionally substituted with lower alkyl groups with 1–5 carbon atoms In a presently preferred embodiment of the intention a prostaglandin derivative to be used according to this invention is a 13,14-dihydro-17-phenyl-18,19,20-trinor-$PGE_2$-alkyl ester, in which the alkyl chain has 1–10 carbon atoms, and especially 1–6 atoms, for instance methyl, ethyl, propyl, isopropyl, butyl, isobutyl, neopentyl or benzyl esters.

The invention will in the following be illustrated with a preferred method for the synthesis of a suitable derivative and by comparative biological experiments.

BRIEF DESCRIPTION OF THE DRAWING

The drawing shows a reaction scheme for the preparation 13,14-Dihydro-17-phenyl-18,19,20-trinor $PGE_2$-isopropyl ester referred to in the description of the synthesis thereof.

PREPARATION OF 13,14-DIHYDRO-17-PHENYL-18,19,20-TRINOR $PGE_2$-isopropyl ester 13

Step a

Figure 1:
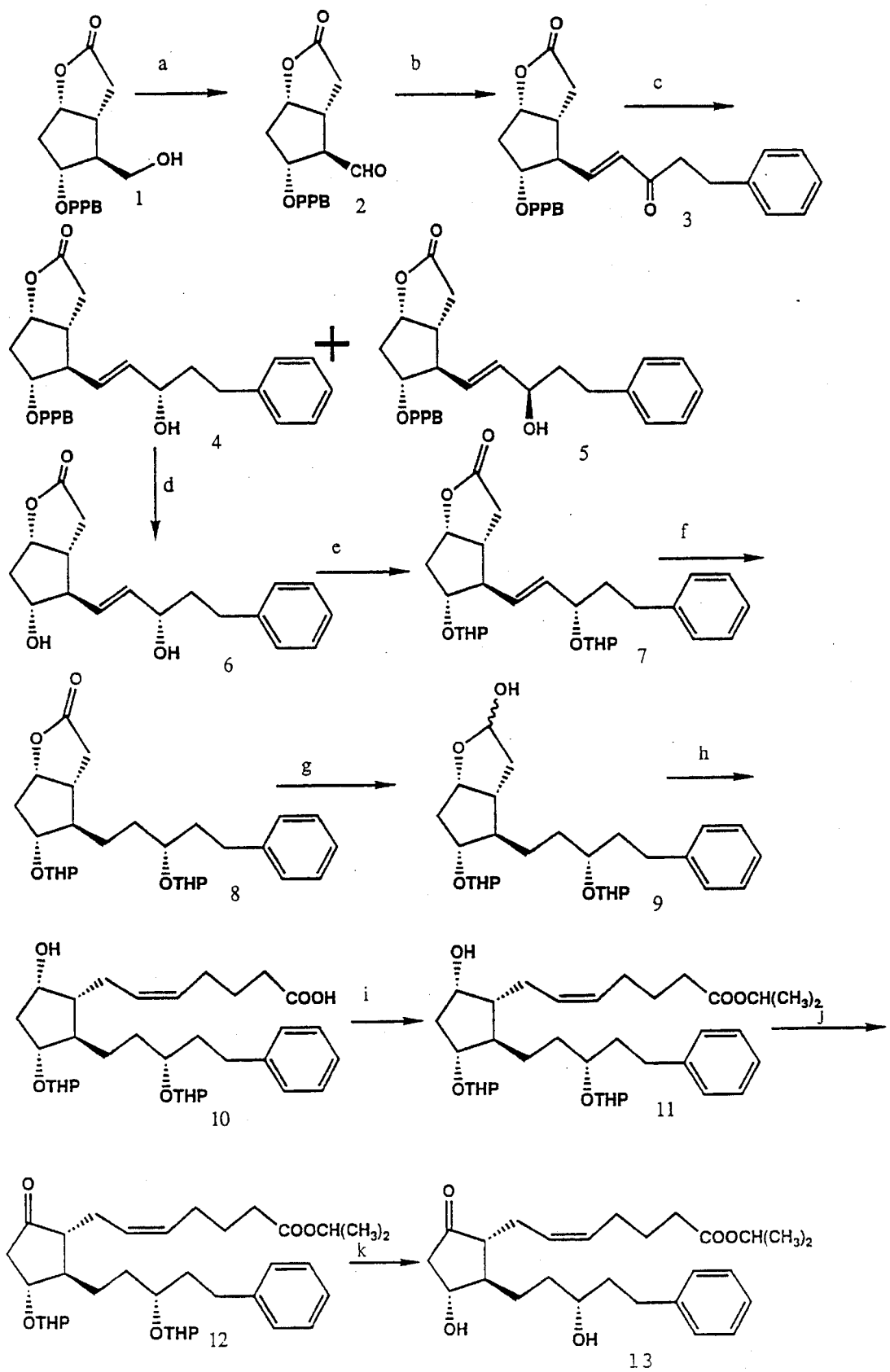

1. Preparation of 1-(S)-2-oxa-3-oxo-6R-formyl-7R-(4-phenylbenzoyloxy) cis-bicyclo-[3,3,0]-octane 2

A mixture of alcohol 1 (20 g, 56,8 mmol), DCC (35,1 g, 170,0 mmol), DMSO (35,5 g, 454 mmol) and DME (80 ml) was stirred mechanically under nitrogen at ambient temperature for 5 min (Pfitzner et al (1965), and thereafter one portion of orthophosphoric acid 85% (3,3 g, 28,4 mmol) was added. After stirring for 2 h, at which time the reaction was completed (TLC monitoring), the resultant precipitate was filtered off and washed with DME to give the unstable crude aldehyde 2. $R_f$ =0,32 (silica gel, EtoAc:toluene 2:1).

Step a

2. Preparation of 1-(S)-2-oxa-3-oxo-6R-[3-oxo-5-phenyl-1-trans-pentenyl] -7R-(4-phenylbenzoyloxy) cis-bicyclo-[3,3,0]-octane 3

To a suspension of NaH (2,2 g, 74 mmol) (80% washed with n-pentane to remove mineral oil) in DME (150 ml) under nitrogen, was added dropwise dimethyl-2-oxo-4-phenyl-butyl-phosphonate (20,9 g, 81,6 mmol) prepared according to the method described by Corey et al (1966), in DME (50 ml) and stirred mechanically for 1 h at room temperature. The mixture was then cooled to – 10° C. and a solution of the crude aldehyde 2 was added dropwise. After 15 min at 0° C. and 1 h at room temperature (TLC monitoring) the reaction mixture was neturalized with glacial acetic acid, the solvent was removed and to the residue was added ethyl acetate (150 ml), washed with water (50 ml) and brine (50 ml). The organic layer was dried over unhydrous sodium sulfate. This solvent was then removed in vacuo and the resulting white precipitate was filtered and washed with cold ether. The title compound 3 was a crystalline substance mp 134–135,5; yield= 28 g (63%); Rf= 0,55 (silica gel, EtoAc: toluene 2:1)

$[\alpha]^{20}_D$=–116 (C=1,26, $CH_3CN$)

$^1$-NMR($CDCl_3$/TMS):delta=2,9(8H m) , 5,1 (1H t), 5,3 (1H m), 6,2 (1H d), 6,7 (1H dd), 7,1–7,6 (10H m), 8,1 (4H d).

Step c

3. Preparation of 1-(S)-2-oxa-3-oxo-6R-(3S-hydroxy-5-phenyl-1-trans-pentenyl)- 7R-(4-phenylbenzoyloxy) cis-bicyclo-[3,3,0]-octane 4

To a stirred solution of lithium tri-sec-butylborohybride (0,5 g, 13,55 mmol) (Brown et al (1972) in dry ether (30 ml) at – 120° C. under nitrogen was added a solution of enone 3 (5 g, 10,325 mmol) (in THF:ether 1:1) (20 ml) cooled to –78° C. within a period of one minute after TLC monitoring (1 h). The reaction mixture was poured into a mixture of water, sodium bisuphate and brine. The temperature was raised to 0 C, more water added, and the mixture transferred to a separatory funnel. Ethyl acetate (50 ml) was added. The organic phase was dried ($Na_2SO_4$), concentrated and subjected to flash column chromatography (silica gel, ethyl acetate) furnishing ! as a white crystalline product; yield= 3 g (60%); Rf= 0,5 (silica gel, EtoAc) $[\alpha]^{25}_D$=–101 59 (C= 0,69 $CH_3CN$). $^1$H-NMR ($CDCl_3$/TMS) :delta= 4,1 (1H m) , 5,5 (2H m) , 5,3 (1H m) , 7,1–7,6 (10H m), 8,1 (4H d).

Step d

4. Preparation of 1-(S)-2-oxa-3-oxo-6R-(3S-hydroxy-5-phenyl-1-trans-pentenyl)- 7R-hydroxy) cis-bicyclo-[3,3,0]-octane To a solution of lactone 4 (9,8 g, 20,0 mmol) in methanol (100 ml) was added potassium carbonate (1,7 g, 12 mmol), and stirred at ambient temperature for 3 h (TLC monitoring). The mixture was neutralized with 1 N HCl (40 ml) and the product extracted with ethyl acetate (2×50 ml). The organic phase was dried ($Na_2SO_4$) and evaporated to dryness. The crude product was subjected to flash column chromatography (silica gel, ethyl acetate:acetone 1:1). The title compound 6 was obtained as a colourless oil; yield= 4,9 g (85%). Rf= 0,31 (silica gel, EtoAc) .

$[\alpha]^{20}_D = -20,48$ (C= 2,5 $CH_3CN$).

$^1$H-NMR ($CDCl_3$/TMS) :delta= 1,9 (2H m) , 2,7 (4H m) , 3,9 (1H m) , 4,1 (1H m), 4,9 (1H m), 5,5 (2H m), 5,6 (1H m), 7,2 (5H m).

Step e

5. Preparation of 1-(S)-2-oxa-3-oxo-6R-[3S-(2-tetrahydropyranyloxy)- 5-phenyl-l-trans-pentenyl-7R-(2-tetrahydropyranyloxy)-cis-bicyclo-[ 3,3,0]-octane 7

To a stirred solution of DIOL 6 (3,3 g, 11,6 mmol) and dihydropyran (4,4 g, 52 mmol) in dichloromethane (50 ml) under nitrogen, was added pyridinium-4-toluenesulfonate (0,3 g, 1,15 mmol). The mixture was allowed to stand at room temperature for 16 h (TLC monitoring), whereafter the solution was remoded in vacuo. The residue was diluted with ether (100 ml), transferred to a separatory funnel, and washed with brine (30 ml), where upon the organic layer was dried ($Na_2SO_4$). When concentrated in vacuo 7 was obtained as a colourless oil, which was used directly for the next step.

$R_f$= 0,57 (silica gel, ether).

Step f

6. Preparation of 1-(S)-2-oxa-3-oxo-6R-[3R-(2-tetrahydropyranyloxy)- 5-phenyl]-l-pentyl-7R-(2-tetrahydropyranyloxy)-cis-bicyclo-[ 3,3,0]-octane 8

The above lactone 7(5,5 g, 11,7 mmol) was dissolved in THF or ethanol (100 ml) and stirred under hydrogene atmosphere for 4 h (TLC monitoring) in the presence of Pd-c catalyst (2,1 g). Filtration through celite pad followed by concentration gave pure 8 as a colourless oil which was used directly for the next step; yield= 5,3 g (97%); $R_f$=0,39 (silica gel, ether: ethyl acetate: acetic acid 50: 1: 0,2 ) . $^1$H-NMR ($CDCl_3$/TMS)delta= 4,6 (1H m), 4,9 (1H m), 7,2 (5H m).

Step g

7. Preparation of 1-(S)-2-oxa-3-hydroxy-6R-[3R-2-tetrahydropyranyloxy)- 5-phenyl-l-pentyl]-7R-(2-tetrahydropyranyloxy)-cis-bicyclo-[ 3,3,0]-octane 9

To a stirred solution of the above lactone 8 (5,5 g, 11,7 mmol) in dry toluene (60 ml) at −78 ° C. was added a solution of diisobutylalbumiun hybride (1,5 M i toluene. 2,0 g, 14,0 mmol) dropwise. After stirring for 2 h (TLC monitoring) the reaction mixture was quenched by addition of methanol (60 ml). The temperature was raised to room temperature and stirring continued for 3.4 h. After filtration, the filtrate was concentrated in vacuo. The corresponding lactol 9 was obtained as a colourless oil; yield= 3,8 g (76%); $R_f$=0,42 (silica gel, EtoAc).

Step h

8. Preparation of 11,15-bistetrahydropyranyloxy-13,14-dihydro- 17-phenyl-18,19,20-trinor-$PGF_2$ 10

Sodium methylsulfinylmethide (4,1 g, 40,9 mmol) freshly prepared from sodium hybride and DMSO was added dropwise to a solution of 4-carboxybutyl triphenylphosphonium bromide (5,5 g, 20,5 mmol) in DMSO (40 ml). To the resultant red solution of ylide was added dropwise a solution of the lactol 9 (2,3 g, 5,9 mmol) in DMSO (15 ml) and the mixture was stirred for 1 h (TLC monitoring). The reaction mixture was diluted with ice and water (50 ml), acidified with 1 N HCl and extracted with ethyl acetate, where upon the organic layer was dried over ($Na_2SO_4$), and concentrated in vacuo furnishing 10 as a slightly yellow oil which is used directly for the next step. $R_f$= 0,38 (silica gel, EtoAc).

Step i

9. Preparation of 11,15-bistetrahydropyranyloxy-13,14-dihydro 17-phenyl-18,19,20-trinor-$PGF_2$ -isopropyl ester 11

To a stirred solution of the crude product 10 (3,27 g, 5,9 mmol) in acetone (25 ml) at 0 ° c, was added DBU (6,25 g, 41,0 mmol) dropwise, and the mixture was allowed to warm up to room temperature, followed by dropwise addition of isopropyliodide (7,3 g, 35,2 mmol) with continuously stirring for 4 h (TLC monitoring). The mixture was transferred to a separatory funnel, diluted with ether (100 ml), washed with brine (30 ml), citric acid 3% (2×25 ml) and sodium hydrogen carbonate 5% (2×25 ml), dried ($Na_2SO_4$) and evaporated. After flash column chromatography (silica gel, ether) the corresponding ester 11 was obtained as a colourless oil; yield= 2,0 g (57%); Rf= 0,58 (silica gel, ether).

IR(neat)= V= 3521, 2939, 2870, 2327, 1730, 1685, 1454, 1352, 246, 1201, 1111, 1024.

$^1$H-NMR ($CDCl_3$/TMS):delta= 4,6 (1H m), 5,0 (1H m), 5,4 (2H m), 7,2 (ss m).

Step j

10. Preparation of 11,15-bistetrahydropyranyloxY-13,14-dihydro- 17-phenyl-18,19,20-trinor-$PGE_2$-isopropyl ester 12

To a stirred solution of the above bistetrahydropyranylether 11 (1,0 g, 1,66 mmol) in dichloromethane (10 ml) was added pyridinium chloro chromate (1,4 g, 6,66 mmol) adsorbed on alumina. After completion of the reaction ether (50 ml) was added, the product filtered, and washed with ether (50 ml). The ether layer was washed with sodiumbicarbonate 5% (2×30 ml), dried on $Na_2SO_4$ and evaporated in vacuo. The crude product was subjected to flash chromatography (silica gel, ether) furnishing 12 as a colourless oil; yield= 43%

Step k

11. Preparation of 13,14-dihydro-17-phenyl-18,19,20-trinor $PGE_2$-isopropyl ester 13

To a stirred solution of the above ester 12 (0,4 g, 0,67 mmol) in ethanol, was added pyridinium-4-toluenesulfonate (16,8 mg, 0,07 mmol) and the mixture was warmed to 50°–55° C. over a period of 3 h at which time the reaction was completed (TLC monitoring). The mixture was concentrated in vacuo, the residue diluted with ethyl acetate (50 ml), washed with water (20 ml) and thereafter brine (20 ml). The organic layer was dried and after flash chromatography (silica gel, ethylacetate: ether 2:1), the pure product 13 was obtained as a colourless oil; yield= 78%.

$R_f$=0,31 (silica gel, ethylacetate)

$^1$H-NMR ( $CDCl_3$/TMS ): delta= 1,2 (6H d), 3,6 (1H m), 4,1 (1H m), 5,0 (1H, m), 5,3 (2H m), 7,2 (5H m)

In comparative biological experiments the following methods have been used:

Sensory nerve irritation has been studied using the cat eye as a behavioural model. The prostaglandin to be studied has been applied topically to the eye of unanesthetized cats as an eye drop and the degree of lid closure of the eye has been followed for a certain period of time. No lid closure has been graded as 0 irritation and total lid closure as 3. Since nociceptive sensory nerves are closely reminiscent in different tissues and organs the eye may serve as a reasonably good model for the gastric tract with respect to pain sensation.

The sensory irritating effect of the new prostaglandin derivatives represented by 13,14-dihydro-17-phenyl-18,19, 20-trinor PGE$_2$-isopropylester when compared with a corresponding ester of the naturally occurring prostaglandin gave the following results:

| Derivative | Dose (μg) | Number of exp. | Score of irritation. |
|---|---|---|---|
| PGE$_2$-isopropyl ester | 1 | 6 | 3.0 ± 0.0 |
| 13,14-dihydro-17-phenyl-18,19,20-trinor-PGE$_2$-isopropyl ester | 1 | 6 | 0.3 ± 0.2 | and there is accordingly a remarkable improvement of the results obtained using the new derivative.

The diarrheagenic effect has been studied in unanesthetized rats. The prostaglandin to be tested has been dissolved in peanut oil and has been applied directly into the stomach through orogastric gavage. The rats were fasted for 24 hours before the test. After the administration of the test substance the animals were studied for 8 hours.

In two series of experiments resp. 6 and 15 mg/kg of 13,14-dihydro- 17-phenyl-18,19,20-trinor-PGE$_2$-isopropyl ester were given to a group of 3 rats and in both cases the score of diarrhea was 0.0. That means that one of the most serious problems with the prior art substance is completely eliminated by using the new derivatives.

The animals were then sacrificed and the whole intestine from duodenum to rectum was inspected. The thickness of the mucus in the ventricle was determined by taking biopsies with a special knife enabling perpendicular sections against the wall of the ventricle. The sections were mounted in a moist chamber and were photographed through a microscope so that the thickness of the mucous layer could be visualized. The thickness of the mucous layer was then measured from the pictures.

A group of 7 animals treated with 13,14-dihydro-17-phenyl- 18,19,20-trinor-PGE$_2$-isopropyl ester were found to have a mucous layer thickness of 151±44 μm (P-value 0.058), while a control group of 9 animals receiving only the vehicle (peanut oil) had a corresponding mucous layer thickness of 114±44 μm. This experiment clearly demonstrates the positive effect of substances according to the present invention.

The new prostaglandin derivatives, accordingly exhibit unique properties in that they cause practically no irritating effect, as naturally occurring prostaglandins do, and no diarrheagenic effect even at very high dose levels while retaining their therapeutically beneficial effect. Typically the new prostaglandin derivatives can be administered as capsules or tablets orally but also as liquid, e.g. in the form of an oil. Sustained release formulations can also be used. Preferably derivatives of PGE$_2$ are employed but also corresponding analogues of PGE$_1$ are believed possible.

Any suitable carrier material may be combined with the above new derivatives as long as there is no interference with the action of the derivatives.

A typical dose of these new prostaglandin derivatives is 0.001–1 mg/kg body weight (b.w.), preferably 0.005–0.5 mg/kg b.w., to be administered orally, one to three times daily.

Since prostaglandins are known to prevent ulcer formation in the gastrointestinal tract during treatment with nonsteroidal anti-inflammatory agents such as e.g. aspirin, indomethacin, diclofenac, piroxicam, naproxen, and ibuprofen it is also possible to use the new analogues during such treatment in combination with the nonsteroidal anti-inflammatory agent.

Typically the dose in such treatment is approximately the same as that mentioned above.

References

Pfitzner (1965); J. Am. Chem. Soc. 87, pp 5670–5678.
Corey (1966); J. Am. Chem. Soc. 88., p 5654.
Brown (1972); J. Am. Chem. Soc. 94, pp 7159–7161.

We claim:

1. A method for treating a person having duodenal or gastric ulcer, gastritis or related alimentary diseases comprising administering a prostaglandin derivative having the formula wherein
R is an alkyl chain with 1–10 carbon atoms,
RI is O or CH$_2$,
RII is H, OH, lower alkyl or halogen,
X is a carbon chain with 1–9 atoms in the chain, optionally interrupted by one heteroatom O, N or S, and
RIII is a ring structure selected from the group consisting of a phenyl group which is unsubstituted or has one or more substituents selected from C1–C5 alkyl groups, C1–C4 alkoxy groups, trifluoromethyl groups, C1–C3 aliphatic acylamino groups, nitro groups, halogen atoms, and a phenyl group;
an aromatic heterocyclic group having 5–6 ring atoms; or
a cycloalkane or a cycloalkene with 3–7 carbon atoms in the ring, optionally substituted with lower alkyl groups with 1–5 carbon atoms.

2. A method according to claim 1 wherein said derivative is administered at a dose of 0.001–1 mg/kg body weight one to three times daily.

3. A method according to claim 1, wherein X is interrupted by one heteroatom O, N or S.

4. A method according to claim 3 wherein said derivative is administered at a dose of 0.001–1 mg/kg body weight one to three times daily.

5. A method according to claim 1, wherein X is interrupted by an oxygen atom.

6. A method according to claim 5 wherein said derivative is administered at a dose of 0.001–1 mg/kg body weight one to three times daily.

7. A method according to claim 1, wherein RIII is an aromatic heterocyclic group selected from the group consisting of thiazole, imidazole, pyrrolidine, thiopene and oxazole.

8. A method according to claim 1, wherein R is an alkyl chain with 1–6 carbon atoms.

9. A method according to claim 1, wherein RII is lower alkyl with 1–3 carbon atoms, Cl, Br or F.

10. A method according to claim 1, wherein X is a carbon chain with 2–6 atoms in the chain.

11. A composition for treating a person having duodenal or gastric ulcer, gastritis or related alimentary diseases consisting of a PGE derivative of the formula

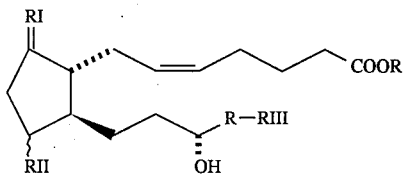

wherein
R is an alkyl chain with 1–10 carbon atoms,
RI is O or $CH_2$,
RII is H, OH, lower alkyl or halogen,
X is a carbon chain with 1–9 atoms in the chain, optionally interrupted by one heteroatom O, N or S, and
RIII is a ring structure selected from the group consisting of a phenyl group which is unsubstituted or has one or more substituents selected from C1–C5 alkyl groups, C1–C4 alkoxy groups, trifluoromethyl groups, C1–C3 aliphatic acylamino groups, nitro groups, halogen atoms, and a phenyl group;

an aromatic heterocyclic group having 5–6 ring atoms; or a cycloalkane or a cycloalkene with 3–7 carbon atoms in the ring, optionally substituted with lower alkyl groups with 1–5 carbon atoms;

in a physiologically acceptable carrier.

12. A composition according to claim 11 wherein said PGE derivative is 13,14-dihydro-17-phenyl-18,19,20-trinor-$PGE_2$-alkyl ester, wherein the alkyl chain has 1–10 carbon atom.

13. A composition according to claim 11 wherein said PGE derivative is 13,14-dihydro-17-phenyl-18,19,20-trinor-$PGE_2$ isopropylester.

14. A composition according to claim 11, wherein X is interrupted by one heteroatom O, N or S.

15. A composition according to claim 11, wherein X is interrupted by an oxygen atom.

16. A composition according to claim 11, wherein RIII is an aromatic heterocyclic group selected from the group consisting of thiazole, imidazole, pyrrolidine, thiopene and oxazole.

17. A composition according to claim 11, wherein R is an alkyl chain of 3–10 carbon atoms.

18. A method according to claim 11, wherein R is an alkyl chain with 1–6 carbon atoms.

19. A method according to claim 11, wherein RII is lower alkyl with 1–3 carbon atoms, Cl, Br or F.

20. A method according to claim 11, wherein X is a carbon chain with 2–6 atoms in the chain.

* * * * *

UNITED STATES PATENT AND TRADEMARK OFFICE
CERTIFICATE OF CORRECTION

PATENT NO. : 5,510,382  Page 1 of 2
DATED : April 23, 1996
INVENTOR(S) : Stjernschantz et al.

It is certified that error appears in the above-indentified patent and that said Letters Patent is hereby corrected as shown below:

On title page, under [*], change "June 29, 2010" to read
--The term of this patent shall not extend beyond the expiration
date of Pat. No. 5,223,537.--

At column 3, lines 5-10, please change the formula by deleting "R—RIII" and inserting —X—RIII—.

At column 4, line 2, please delete "$R_y$" and insert —$R_f$—.

At column 4, line 4, please delete "a" and insert —b—.

At column 4, line 15, please delete the "." following C.

At column 4, line 17, please delete the "." following C.

At column 4, line 25, please delete "$R_y$" and insert —$R_f$—.

At column 4, line 41, please delete the "." following C.

At column 4, line 48, please delete "!".

At column 4, line 49, please delete "$R_y$" and insert —$R_f$— ; insert —.— after "Ac)"; and insert —,— after "101".

At column 4, line 57, please insert —6— after "octane".

At column 4, line 67, please delete "$R_y$" and insert —$R_f$—.

At column 5, line 21, please delete "$R_y$" and insert —$R_f$—.

At column 6, line 7, please insert — — — after "dihydro".

At column 6, line 9, please delete "c" and insert —C—.

At column 6, line 19, please delete "$R_y$" and insert —$R_f$—.

At column 6, line 21, please delete "246" and insert —1246—.

At column 6, line 23, please delete "ss" and insert —5H—.

At column 6, line 27, please delete "Y" and insert —y—.

UNITED STATES PATENT AND TRADEMARK OFFICE
CERTIFICATE OF CORRECTION

PATENT NO. : 5,510,382
DATED : April 23, 1996
INVENTOR(S) : Stjernschantz et al.

It is certified that error appears in the above-indentified patent and that said Letters Patent is hereby corrected as shown below:

At column 6, line 48, please delete "." after "C".
At column 6, line 55, please delete "$R_f$" and insert --$R_f$--.

Signed and Sealed this

Third Day of December, 1996

BRUCE LEHMAN

Attest:

Attesting Officer

Commissioner of Patents and Trademarks